United States Patent
Michielli (10) Patent No.: US 10,456,267 B2
(45) Date of Patent: Oct. 29, 2019

(54) LATERAL CAGE STABILIZATION

(75) Inventor: Michael Michielli, Medway, MA (US)

(73) Assignee: Medos International Sarl, Le Locle (CH)

( * ) Notice: Subject to any disclaimer, the term of this patent is extended or adjusted under 35 U.S.C. 154(b) by 540 days.

(21) Appl. No.: 13/303,533

(22) Filed: Nov. 23, 2011

(65) Prior Publication Data

US 2013/0131809 A1    May 23, 2013

(51) Int. Cl.
*A61F 2/44* (2006.01)
*A61B 17/04* (2006.01)
*A61F 2/46* (2006.01)
*A61B 17/06* (2006.01)

(52) U.S. Cl.
CPC ........ *A61F 2/4455* (2013.01); *A61B 17/0401* (2013.01); *A61B 17/0469* (2013.01); *A61B 17/0487* (2013.01); *A61B 2017/044* (2013.01); *A61B 2017/0409* (2013.01); *A61B 2017/0414* (2013.01); *A61B 2017/0427* (2013.01); *A61B 2017/0437* (2013.01); *A61B 2017/0445* (2013.01); *A61B 2017/0496* (2013.01); *A61B 2017/06176* (2013.01); *A61F 2/4611* (2013.01)

(58) Field of Classification Search
CPC ...... A61F 2/4455; A61F 2/446; A61F 2/4465; A61F 2/447; A61F 2/4611; A61B 2017/0409; A61B 2017/0414; A61B 2017/0427; A61B 2017/0437; A61B 2017/044; A61B 2017/0445; A61B 2017/0496; A61B 2017/06176; A61B 17/0401; A61B 17/0469; A61B 17/0487

USPC .......................................... 623/17.11–17.16
See application file for complete search history.

(56) References Cited

U.S. PATENT DOCUMENTS 5,178,629 A * 1/1993 Kammerer ......... A61B 17/0469
606/224
5,290,281 A * 3/1994 Tschakaloff ....... A61B 17/8085
219/229
5,294,395 A * 3/1994 Broyer .................... A61L 17/04
264/178 F
5,370,661 A * 12/1994 Branch .............. A61B 17/0401
606/232

(Continued)

FOREIGN PATENT DOCUMENTS

EP      1297789     4/2003
EP      1917915     5/2008

(Continued)

OTHER PUBLICATIONS

Seung-Ho Kim, M.D. and Kwon-Ick Ha, M.D., Ph.D.; Technical Note the SMC Knot—A New Slip Knot With Locking Mechanism; Arthoscopy: The Journal of Arthoroscopic and Related Surgery, vol. 16, No. 5 Jul.-Aug. 2000, pp. 563-565.*

(Continued)

*Primary Examiner* — Ellen C Hammond
*Assistant Examiner* — Tessa M Matthews (57) ABSTRACT

A kit for stabilizing an intervertebral disc space, wherein the kit includes a cage, a suture and a plurality of suture anchors. The suture anchors are pressed into the anterior faces of the vertebral bodies holding the cage, while the ends of the suture are formed into a loose, preformed Giant Knot to allow their tightening to be accomplished through a minimally invasive portal.

5 Claims, 12 Drawing Sheets

(56) References Cited

U.S. PATENT DOCUMENTS

| | | | | |
|---|---|---|---|---|
| 5,735,877 | A * | 4/1998 | Pagedas | A61B 17/0487 606/232 |
| 5,904,704 | A * | 5/1999 | Goble | A61B 17/0401 606/232 |
| 6,004,326 | A * | 12/1999 | Castro | A61B 17/025 606/99 |
| 6,015,428 | A * | 1/2000 | Pagedas | A61B 17/0483 606/232 |
| 6,093,205 | A * | 7/2000 | McLeod | A61F 2/442 606/247 |
| 6,248,106 | B1 * | 6/2001 | Ferree | 606/263 |
| 6,596,015 | B1 | 7/2003 | Pitt | |
| 6,645,211 | B2 * | 11/2003 | Magana | 606/247 |
| 7,156,848 | B2 * | 1/2007 | Ferree | 606/261 |
| 7,344,539 | B2 | 3/2008 | Serhan | |
| 7,582,105 | B2 * | 9/2009 | Kolster | A61B 17/06 606/228 |
| 7,828,850 | B2 * | 11/2010 | Cauthen et al. | 623/17.16 |
| 8,162,993 | B2 * | 4/2012 | Ferree | A61B 17/0401 606/228 |
| 8,449,614 | B2 * | 5/2013 | Ferree | 623/17.16 |
| 8,454,697 | B2 * | 6/2013 | Bentley et al. | 623/17.11 |
| 8,702,733 | B2 * | 4/2014 | Ferree | 606/151 |
| 2002/0107524 | A1 * | 8/2002 | Magana | A61B 17/7059 606/103 |
| 2002/0120270 | A1 | 8/2002 | Trieu | |
| 2005/0216087 | A1 * | 9/2005 | Zucherman et al. | 623/17.16 |
| 2006/0009846 | A1 * | 1/2006 | Trieu et al. | 623/17.11 |
| 2006/0253198 | A1 * | 11/2006 | Myint et al. | 623/17.12 |
| 2007/0073293 | A1 * | 3/2007 | Martz | A61B 17/0401 606/86 A |
| 2007/0191957 | A1 * | 8/2007 | Anderson | A61B 17/0401 623/17.16 |
| 2008/0147063 | A1 * | 6/2008 | Cauldwell | A61B 17/0401 606/60 |
| 2009/0138082 | A1 * | 5/2009 | Reah | A61B 17/7059 623/13.14 |
| 2009/0259260 | A1 | 10/2009 | Bentley | |

FOREIGN PATENT DOCUMENTS

| | | |
|---|---|---|
| WO | WO 2004037094 | 5/2004 |
| WO | WO 2005037150 | 4/2005 |
| WO | WO 2011119865 | 9/2011 |

OTHER PUBLICATIONS

Basim A. Fleega, M.D., and Sherif H. Sokkar, M.D.; Technical Note the Giant Knot: A New One-Way Self-Locking Secured Arthoroscopic Slip Knot; Arthroscopy: The Journal of Arthoroscopic and Related Surgery; vol. 15, No. 4 May-Jun. 1999, pp. 451-452.*

Fleega, The Giant Knot: A New One-Way Self-Locking Secured Arthroscopic Slip Knot, Arthroscopy: The journal of Arthroscopic and Related Surgery, vol. 15, No. 4 May-Jun. 1999, pp. 451-452.

Kim, Arthroscopic Sliding Knot: How Many Additional Half-Hitches Are Really Needed? Arthroscopy. Apr. 2005;21(4):405-11.

Shoulderdoc.co.uk/images/uploads/knots01.jpg Nov. 10, 2011.

* cited by examiner

LATERAL CAGE STABILIZATION

BACKGROUND OF THE INVENTION

The lateral approach is frequently utilized to deliver intervertebral fusion cages to the lumbar spine. In comparison to conventional anterior or posterior approaches to the lumbar spine, the lateral approach is thought to minimize posterior and/or anterior tissue damage as well as reduce surgery time, associated blood loss, vascular damage and infection risk.

However, there appears to be no straightforward method of stabilizing a lateral cage that has been inserted between the opposing vertebral bodies.

U.S. Pat. No. 6,093,205 (McLeod) discloses a prosthesis for replacement of an intervertebral disc of the spine, wherein the prosthesis comprises a block of elastomeric material held under compression by an encapsulating textile fabric. FIG. 5 of McLeod discloses a cat's cradle of suture thread which acts to secure the implant in situ within the disc space and which contributes to the stability of the disc reconstruction by replacing the anterior annulus, which is the fibrous structure across the front of the disc space.

SUMMARY OF THE INVENTION

The present invention enhances lateral cage stabilization by providing a low profile, anterior barrier that is attached to the anterior face of opposed vertebral bodies. The barrier will resist lateral cage expulsion in the anterior direction and can be implanted through the same minimally invasive portal used to implant the lateral cage.

After the lateral cage is placed within the disc space, the surgeon drills a plurality of holes into each of the anterior faces of the adjacent vertebral bodies. The surgeon then places a suture anchor into each of these holes. Each of these anchors are pre-attached to the same high-strength suture. After anchor placement, the suture can be tightened so that even pressure is placed on the cage (and the graft within the cage) and the cage is stabilized.

Therefore, in accordance with the present invention, there is provided a kit for stabilizing an intervertebral disc space, comprising:
a) an intervertebral fusion cage,
b) an expulsion barrier comprising:
   i) a plurality of suture anchors, each anchor having a hollow shaft having an inside surface forming a bore and an outside surface having a bone-engaging surface feature thereon, and
   ii) a suture having a first end portion and a second endportion,
wherein the suture is threaded through the bore of each suture anchor, and
wherein the endportions of the suture forms a slip-knot.

DETAILED DESCRIPTION OF THE INVENTION

Figure 1:
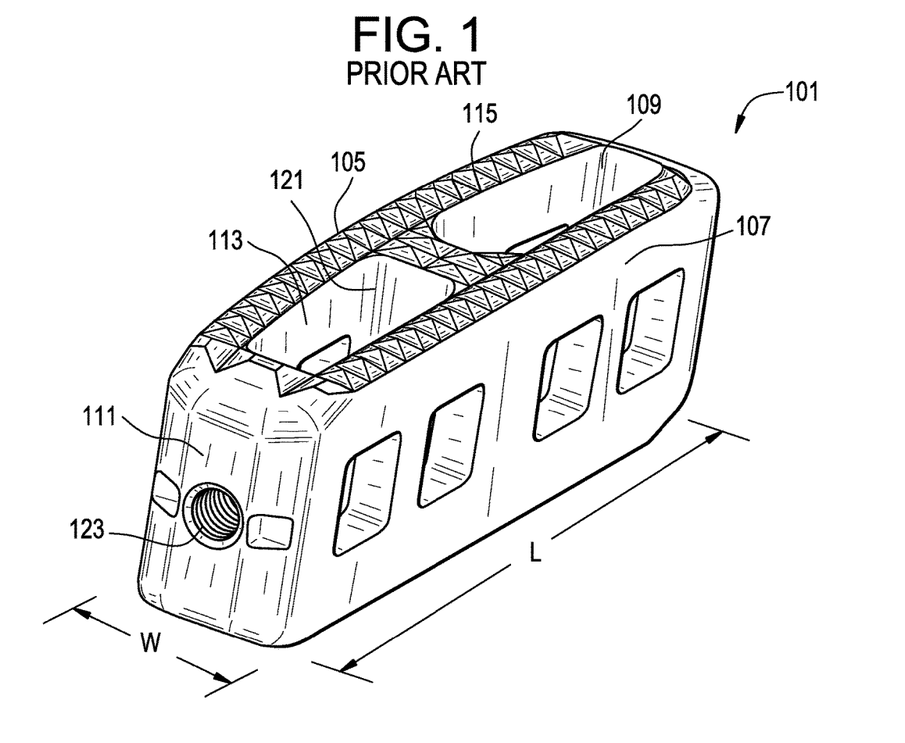
FIG. 1 is a perspective view of a conventional lateral cage.
Figure 2A:
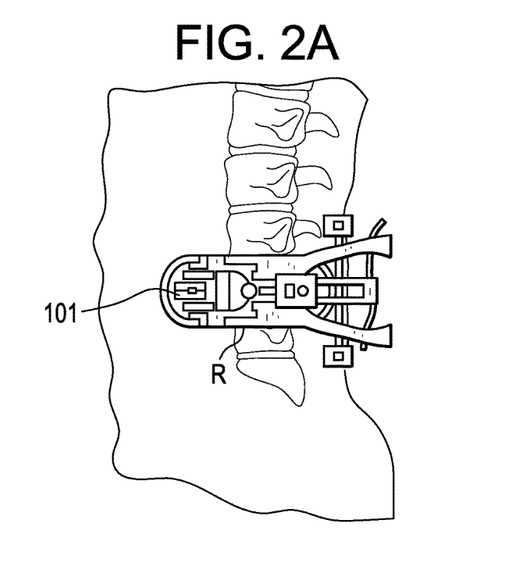
FIG. 2A shows a cage being laterally inserted into a disc space.
Figure 2B:
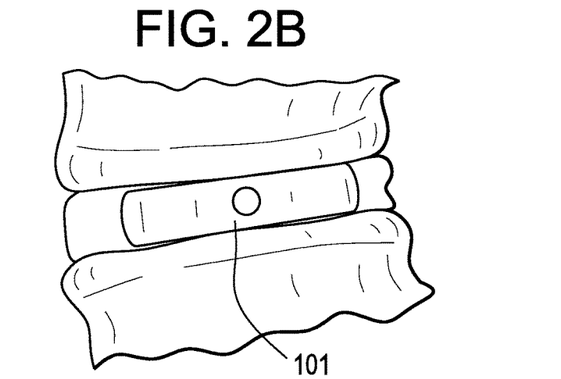
FIG. 2B shows a cage which has been laterally inserted into a disc space
Figure 3:
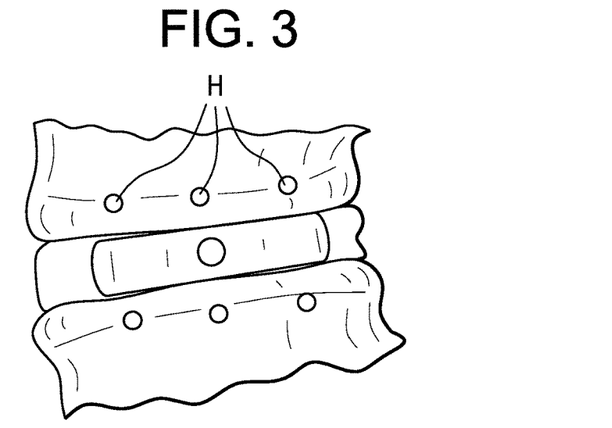
FIG. 3 shows entry holes drilled into the vertebral bodies that are adjacent the implanted lateral cage.
Figure 4A:
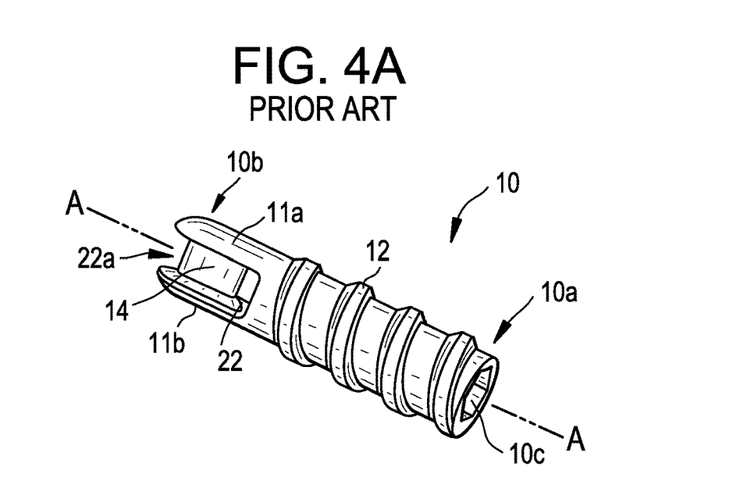
FIG. 4A-4C discloses various views of a conventional suture anchor.
Figure 4B:
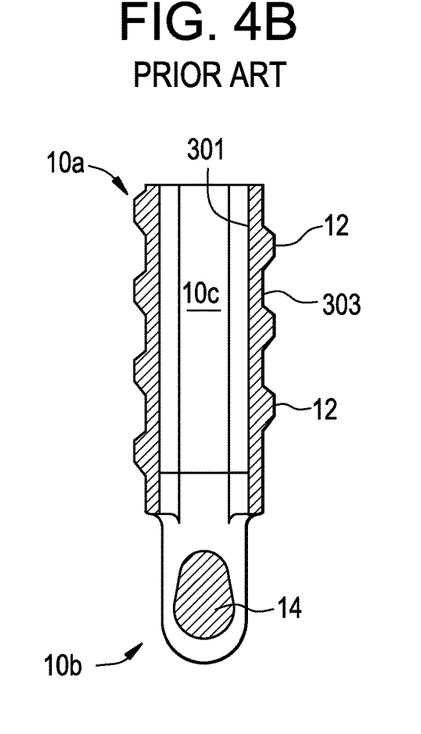
Figure 4C:
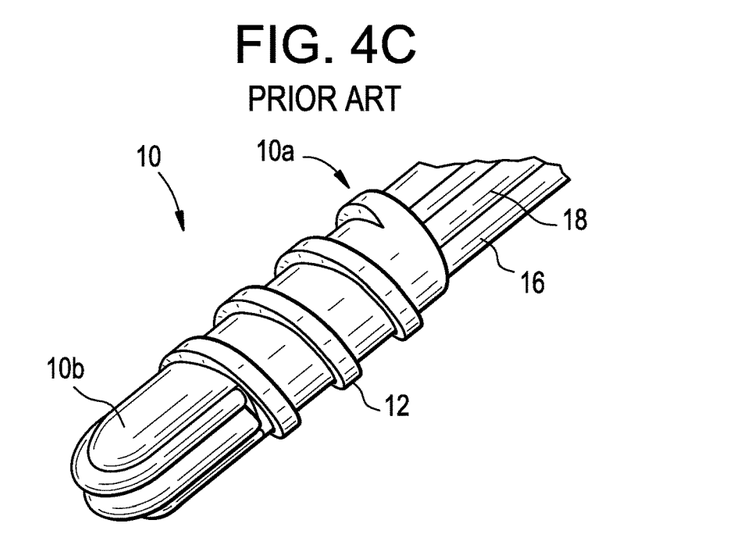
Figure 5A:
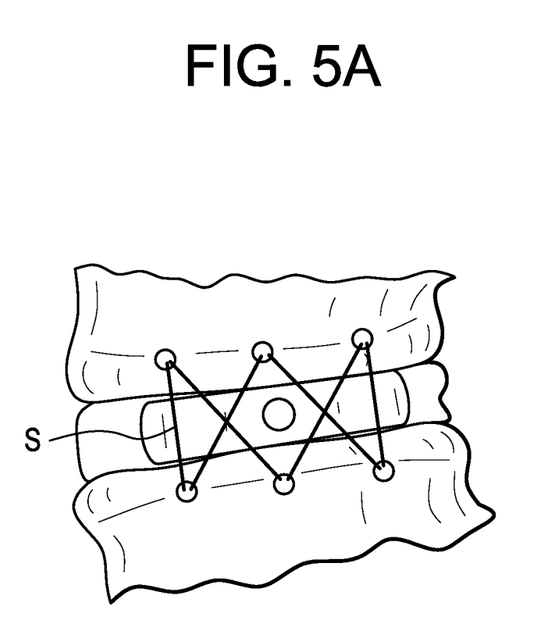
FIG. 5 shows the migration barrier forming a cat's cradle around the implanted lateral cage.

Prior to inserting the cage, a conventional discectomy is performed. In some embodiments, the anterior, contralateral and posterior portions of the annulus fibrosus are preserved. Next, a lateral cage 101, such as that shown in FIG. 1, is selected for insertion into the prepared disc space. FIG. 2A shows the cage 101 being inserted through a refractor R via a lateral approach. FIG. 2B shows a cage 101 which has been laterally inserted into a disc space Next, as shown in FIG. 3, the surgeon drills at least two linearly spaced holes H into a lateral aspect of each of the adjacent vertebral bodies. In FIG. 3, three such holes are shown in each adjacent vertebral body. The surgeon then selects a migration barrier (or "expulsion barrier") comprising a plurality of conventional suture anchors attached to a suture. One such anchor suitable for use in the barrier is shown in FIGS. 4A-4C. The surgeon then presses the suture-connected anchors into their respective holes. The ends of the suture are then pulled to tighten the suture around the cage and the endplates are compressed onto the cage. Next, an operation is performed on the suture to retain its tight fit on the anchors, such as forming a tight knot with the end portions of the suture. If desired, the end portions of the suture S are then cut to form a cat's cradle configuration, as shown in FIG. 5.

Therefore, in accordance with the present invention, there is provided a kit for stabilizing an intervertebral disc space, comprising:
a) an intervertebral fusion cage,
b) an expulsion barrier comprising:
   i) a plurality of suture anchors, each anchor having a shaft having an outside surface having a bone-engaging surface feature thereon, and
   ii) a suture having a first end portion and a second endportion,
wherein the suture anchors are slidably retained on the suture, and
wherein the endportions of the suture forms a slip-knot. In some embodiments, the suture/anchor assembly provides at least about 55 pounds of tensile strength The number of suture anchors as well as their implantation configuration can be adjusted to maximize the stability and compression of the construct.

In some embodiments, the suture anchor is substantially similar to the anchor disclosed in US Patent Publication 2008-0147063 (Cauldwell I) and US Patent Publication 2010-0185238 (Cauldwell II), the specifications of which are incorporated by reference in their entireties.

In one embodiment, the suture anchor is provided having an elongate body with proximal and distal ends and an inner lumen extending therethrough. At least one bone-engaging surface feature, such as a thread or a barb, can be formed on at least a portion of an outside surface thereof for engaging bone. The inner lumen of the elongate body can include a suture-engaging member extending substantially transverse to an axis of the inner lumen and adapted to receive a suture therearound such that a suture can extend around the suture-engaging member and trailing ends of the suture can extend through the inner lumen and out of the proximal end of the elongated body.

FIGS. 4A-4C illustrate one exemplary embodiment of a cannulated suture anchor 10 for anchoring soft tissue to bone. As shown, the suture anchor 10 is in the form of a generally elongate body having proximal and distal ends 10a, 10b with an inner lumen (or "bore") 10c extending therethrough. Thus, each anchor has a hollow shaft having an inside surface 301 forming a bore 10c and an outside surface 303 having a bone engaging surface feature 12 thereon. At least one bone-engaging surface feature 12 can be formed on at least a portion of an external surface thereof for engaging bone. The suture anchor 10 also includes a suture-engaging member 14 disposed within the inner lumen 10c adjacent to the distal end 10b of the suture anchor 10. As shown in FIG. 4C, the suture-engaging member 14 is adapted to receive one or more sutures (two sutures 16, 18 are shown) therearound such that the suture(s) can extend around the suture-engaging member 14 and trailing ends of the suture(s) can extend through the inner lumen 10c and out of the proximal end 10a of the suture anchor 10.

The body of the suture anchor 10 can have a variety of configurations, shapes, and sizes. In an exemplary embodiment, the body is configured to be implanted within a bone tunnel formed in bone, and more preferably it has a size and shape that allows it to be fully engaged through the thickness of the cortical bone. In the illustrated embodiment the body has a generally elongate cylindrical shape with a blunt or rounded distal end 10b to facilitate introduction into a bone tunnel. The proximal end 10a of the body is head-free, as the cannulated configuration of the body allows a driver to be inserted into the inner lumen 10c to drive the suture anchor 10 into bone. As indicated above, the suture anchor 10 can also include one or more bone-engaging surface features formed thereon and adapted to engage bone. While various surface features can be used, such as teeth, ridges, protrusions, etc., in an exemplary embodiment the body can include one or more threads extending therearound. In the illustrated embodiment a single thread extends around the body from the proximal end 10a and it terminates proximal to the distal end 10b. The particular location at which the thread terminates can vary depending on the particular configuration of the suture anchor 10. As will be discussed in more detail below, the illustrated suture anchor 10 can include opposed cut-outs formed in the distal end thereof and the thread can terminate just proximal to the proximal end of the cut-outs.

The suture anchor 10 can also be formed from a variety of materials. In an exemplary embodiment, the material has physical properties that are sufficient to allow a driver to be inserted into the bore 10c of the suture anchor 10 and to be used to drive the suture anchor 10 into bone without damaging the suture anchor 10. The properties of the material will of course depend on the particular configuration of the suture anchor 10. For example, the inner lumen 10c of the suture anchor 10 can have a length that maximizes the torque strength of the suture anchor 10 as well as the amount of surface contact between a driver and the suture anchor 10, thus allowing weaker materials, such as bioabsorbable and/or osteoconductive materials to be used. A person skilled in the art will appreciate that a variety of other materials, including plastics and metals, can be used to form the suture anchor 10.

As previously indicated above, the suture anchor 10 can also include a suture-engaging member 14 formed therein. The suture-engaging member 14 can have a variety of configurations, but in an exemplary embodiment it is adapted to engage one or more sutures that extend through the bore 10c of the suture anchor 10. As shown in FIGS. 4A and 4B, the suture-engaging member 14 is in the form of a post that extends transversely across the bore 10c and between opposed inner sidewalls of the suture anchor 10. The angular orientation of the suture-engaging member 14 relative to a longitudinal axis A of the bore 10c can vary, but in an exemplary embodiment the suture-engaging member 14 extends substantially perpendicular to the longitudinal axis A of the inner lumen 10c. The location of the suture-engaging member 14 can also vary, but in an exemplary embodiment the suture-engaging member 14 is positioned at or adjacent to the distal end 10b of the suture anchor 10. In the embodiment shown in FIGS. 4A and 4B, the suture-engaging member 14 is located just proximal to the distal-most end 10b of the suture anchor 10 so as to form a suture-seating groove 22a in the distal-most end of the suture anchor 10. This recessed configuration of the suture-engaging member 14 can allow a suture(s) disposed around the suture-engaging member 14 to sit flush or sub-flush with the distal end 10b of the suture anchor 10 such that the suture(s) will not interfere with insertion of the suture anchor 10 into bone. A person skilled in the art will appreciate that the suture-engaging member 14 can be integrally formed with the suture anchor 10, i.e., the suture anchor 10 and suture-engaging member 14 can be molded as a single unit or formed from a single piece of material, or the suture-engaging member 14 can be fixedly or removably mated to the suture anchor 10.

As further shown in FIGS. 4A-4C, in order to facilitate positioning of a suture(s) around the suture-engaging member 14, the suture anchor 10 can include one or more cut-outs formed in a sidewall thereof adjacent to the suture-engaging member 14. As best shown in FIG. 4A, in an exemplary embodiment the suture anchor 10 includes a cut-out 22 that begins just proximal to the location of the suture-engaging member 14, and that extends around the distal end 10b of the suture anchor 10 such that the suture anchor 10 includes opposed cut-outs or openings formed on opposed sides of the suture-engaging member 14 and a distal cut-out that defines the suture-seating groove 22a for seating a suture(s). The cut-out 22 can also define opposed distal arms 11a, 11b on the suture anchor 10 that are spaced a distance apart from one another and that have the suture-engaging member 14 extending therebetween.

A person skilled in the art will appreciate that the particular location and configuration of the cut-out 22 can define the particular location and configuration of the suture-engaging member 14, as the cut-out 22 can be formed during manufacturing to create the suture-engaging member 14. Alternatively, the particular location and configuration of the opposed arms 11a, 11b can define the particular location and configuration of the cut-out 22, as the shape and size of the arms 11a, 11b defines the shape and size of the cut-out 22. The location of the suture-engaging member 14 relative to the cut-out 22 and/or arms 11a, 11b will also define the configuration of the distal end of the suture anchor 10, and whether the suture anchor 10 includes a distal groove 22a for seating a suture(s).

As further shown in FIGS. 4A and 4B, the bore 10c of the suture anchor 10 can be adapted to receive a driver therein for driving the suture anchor 10 into bone. While various techniques can be used to facilitate engagement between the bore 10c and a driver mechanism, in an exemplary embodiment the bore 10c, or at least a portion thereof, has an asymmetrical shape that complements a corresponding asymmetrical shape of a driver. The asymmetrical portion preferably extends along a substantial length of the bore 10c so as to maximum surface contact between a driver and the suture anchor. By way of non-limiting example, FIGS. 4A and 4B illustrate a hexagonal cross-sectional shape formed in a proximal portion of the inner lumen 10c for receiving a driver having a corresponding hexagonal drive tip, as will be discussed in more detail below. The hexagonal cross-section extends from the proximal-most end 10a of the suture anchor 10 and terminates just proximal to the proximal end of the cut-out 22.

In another embodiment, rather than having a fixed suture-engaging member 14, the suture anchor can include a suture-engaging member that is rotatably disposed therein. Such a configuration will allow for suture slidability, providing a pulley system to facilitate longitudinal movement of a suture through the inner lumen of the suture anchor. In particular, one or more terminal ends of one or more sutures disposed around the suture-engaging member can be pulled to slide the suture(s) longitudinally within the inner lumen of the suture anchor, and the suture-engaging member can rotate to facilitate such longitudinal movement.

Figure 5B:
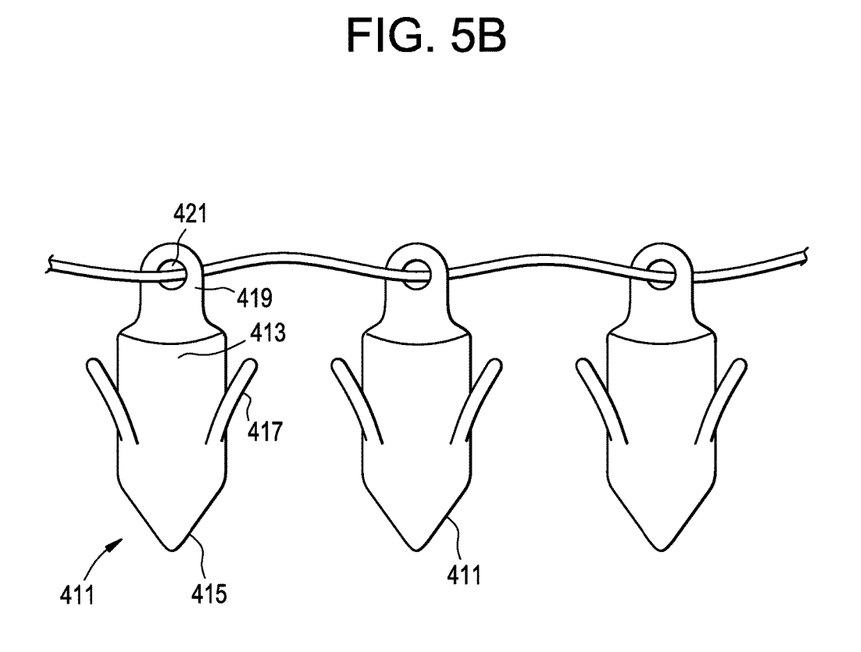

In some embodiments, and now referring to FIG. 5B, the loops of the anchors may be crimped to prevent suture slippage after final placement and tightening. FIG. 5B shows three bone anchors 411 having a body portion 413 having a plurality of barbs thereon, a distal tip 415, and a tapered proximal end portion 419 have a hole 421 therethrough. In use, the suture is passed through each of the proximal holes of these anchors. After the anchors are placed in the bone, the tapered proximal end portion 419 may be crimped to prevent suture slippage after final placement and tightening.

Figure 6:
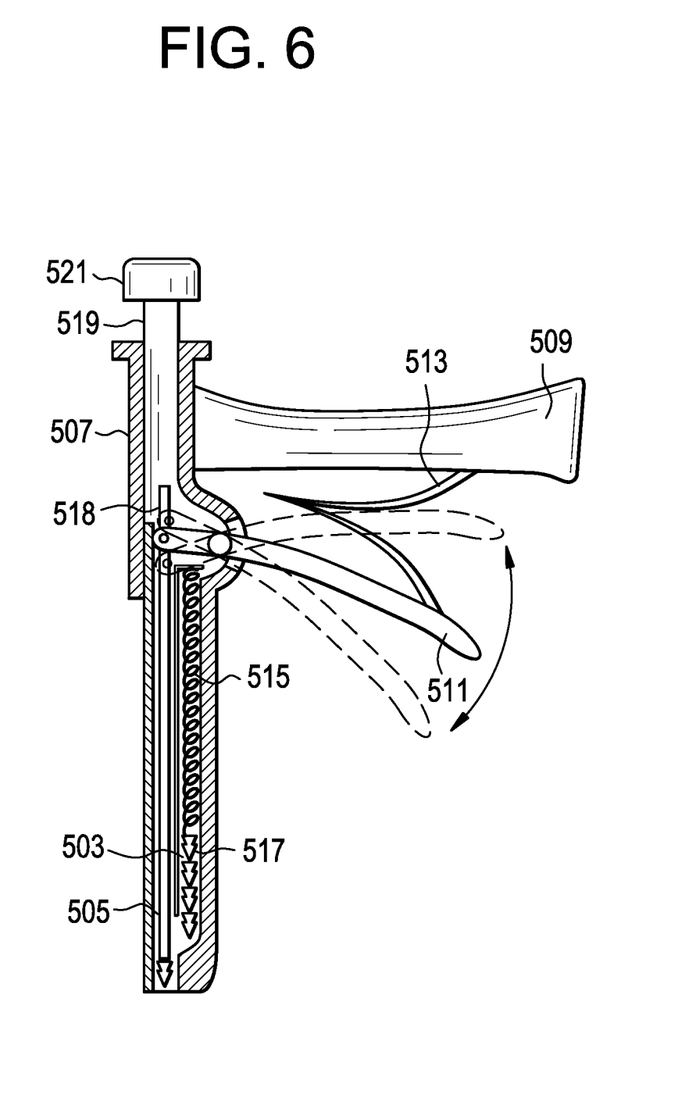
FIG. 6 shows an instrument for implanting the migration barrier of the present invention.

In some embodiments, the plurality of anchors can be delivered through the instrument 501 shown in FIG. 6. The instrument has two parallel barrels 503, 505 mounted on a housing 507. A handle 509 is also mounted on the housing to allow for easy gripping by the surgeon. A trigger 511 is also pivotally mounted on the housing to provide for manual actuation of the device. A spring 513 mounted between the trigger and handle forces the trigger back to its open position in order to provide for repeating actuation. The lower barrel 503 mounted on the housing is adapted for storing the suture anchors 517 therein and for delivering them to the distal end of the instrument. This delivery is accomplished by providing a compression spring 515 in the lower barrel proximal to the series of suture anchors. This spring pushes the anchors distally towards an opening in the upper barrel 505. The lower barrel has a longitudinal slot therein so as to function as a leaf spring. The upper barrel mounted on the housing has a ram 519 provided therein that is actuated by a trigger mechanism. The ram can have a proximal head 521 that can be advanced or pushed in order to advance the ram. The distal end of the ram has a slot 518 for coupling to the trigger. The trigger can be actuated to first advance the ram to thereby push the anchor into the vertebral body, and then to retract the ram to allow the re-loading of the barrel with the next suture anchor.

Figure 7A:
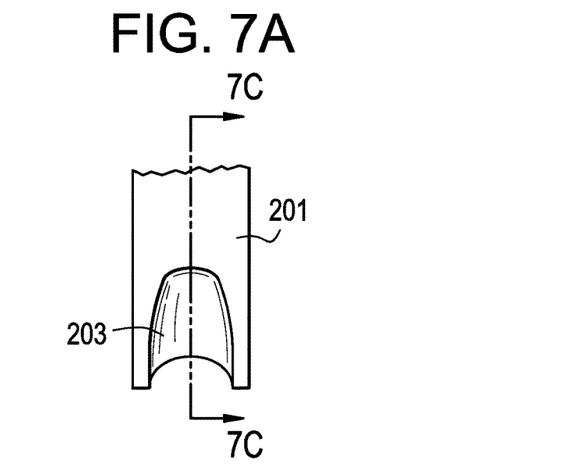
FIG. 7A-7C shows various views of a knot pusher.
Figure 7B:
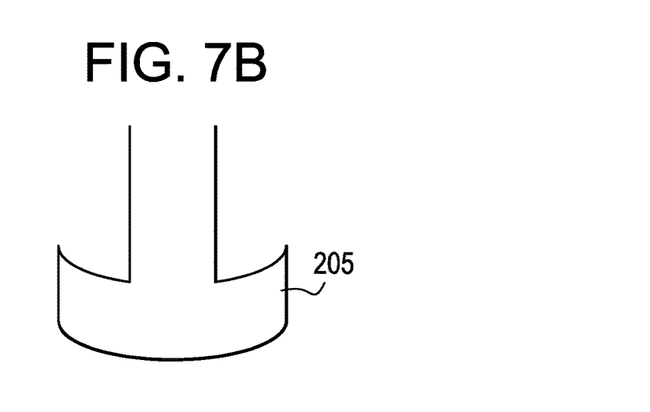
Figure 7C:
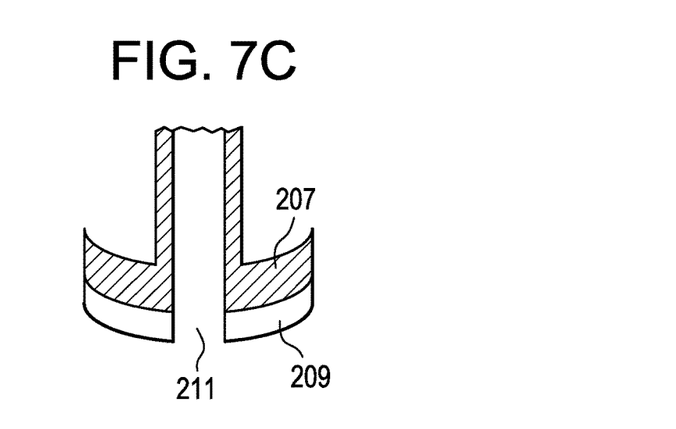

In some embodiments, the instrument that delivers the anchors comprises a built-in "knot pusher". In brief, the knot pusher functions as follows: The surgeon places the knot in the tip of the pusher and pushes down the knot to secure the anchor while pulling tight the suture ends. Examples of some representative views of one preferred knot pusher are shown in FIGS. 7A-7C. FIG. 7A shows the body 201 of the knot pusher feature and its suture recess 203. FIG. 7B displays the flanges 205 of the knot pusher feature. FIG. 7C is a cross-section of the knot pusher, displaying the support material for suture recess, 207, the ridge of the suture recess, 209 and the knot recess 211. The knot pusher can be provided a) at the tip of the delivery instrument, b) adjacent to the tip, or c) as a separate instrument.

In preferred embodiments, the intervertebral cage of the present invention is adapted for insertion into the disc space by a lateral approach.

Now referring back to FIG. 1, there is provided an intervertebral fusion cage 101 having an anterior wall 105, a posterior wall 107, distal 109 and proximal 111 side walls connecting the anterior and posterior walls to form a central throughhole 113, an upper surface 115 adapted for gripping an upper endplate and a lower surface (not shown) adapted for gripping a lower endplate. The central throughhole 113 is bifurcated by a strut 121. The proximal sidewall 111 has a threaded insertion hole 123 adapted for receiving a threaded insertion instrument.

Still referring to FIG. 1, in some embodiments, this lateral cage has a length L:width W ratio of at least 2:1. In some embodiments, this lateral cage has a length:width ratio of at least 2.5:1. In some embodiments, this lateral cage has a length:width ratio of at least 3:1. In some embodiments, the lateral cage has a length of at least 35 mm, preferably at least 40 mm. In some embodiments, the lateral the cage has a width of between 15 mm and 25 mm, preferably between 18 mm and 22 mm. In preferred embodiments, the lateral cage is a CONCORDE LX cage, marketed by DePuy Spine, Raynham, Mass., USA.

In order to stabilize an already-implanted cage, in one embodiment, the surgeon first drills a plurality of holes in the vertebral bodies adjacent the cage. Next, the surgeon inserts a suture anchor (preferably, a GRYPHON P BP™ suture anchor, available from DePuy Mitek, Raynham, Mass. In some embodiments, this suture anchor is modified to be a push-in style (rather than a thread-in style). Preferably, the anchors are pre-threaded with a suture (preferably, an ORTHOCORD™ suture, available from DePuy Mitek, Raynham, Mass.) so that the suture twice passes through the hollow shaft of each suture anchor. The suture slips freely and all six anchors are attached to the same double-stranded suture. In one embodiment, the proximal end of the suture possesses a loose, preformed, slip knot. This loose knot allows the surgeon to simply pull on the ends of the suture to tighten the knot, and thereafter cut the suture ends appropriately. This procedure is amenable to be carried out through a tube.

Figure 8:
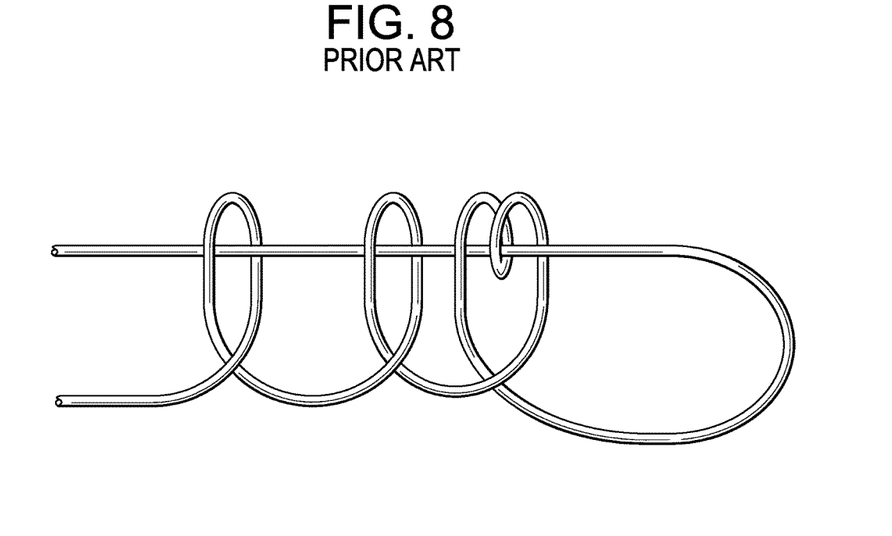
FIG. 8 shows a Giant Knot.

In one embodiment, the slip knot is a Giant Knot, shown in FIG. 8. The Giant Knot is a self-locking slip knot that offers a highly secured knot without the need of additional hitches. However, in some embodiments, additional hitches may be added. It has been used in other areas of arthroscopic, orthopedic surgery. One preferred method of making a Giant Knot is disclosed in Fleega, J. Arthroscopic

Figure 9:
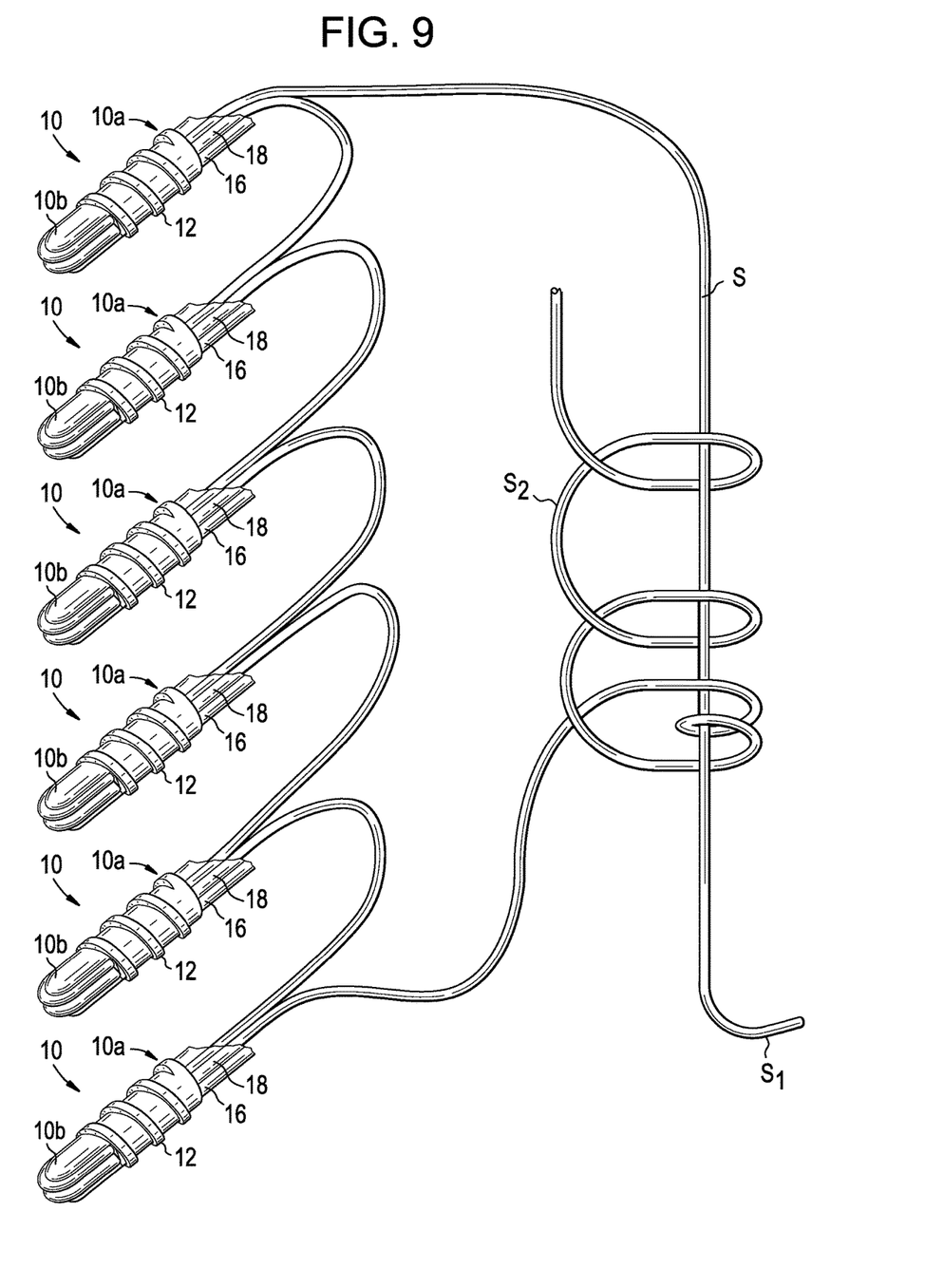
FIG. 9 shows a migration barrier of the present invention formed with a Giant Knot.

*and Related Surgery*, 15, 4 (May-June) 1999, 451-452. An embodiment of a migration barrier of the present invention formed with a Giant Knot is shown in FIG. 9. The migration barrier comprises:

i) a plurality of bone anchors 10, each anchor having a hollow shaft having an inside surface forming a bore and an outside surface having a migration resistance feature thereon, and     ii) a suture S having a first end portion $S_1$ and a second endportion $S_2$,     wherein the suture is threaded through the throughhole of each suture anchor, and wherein the endportions of the suture forms a slip-knot.

In other embodiments, the slip knot can be selected from the group consisting of an SMC Knot, a Snyder Knot, a Duncan Knot, a Field Knot and a Nicky's Knot.

Figure 10:
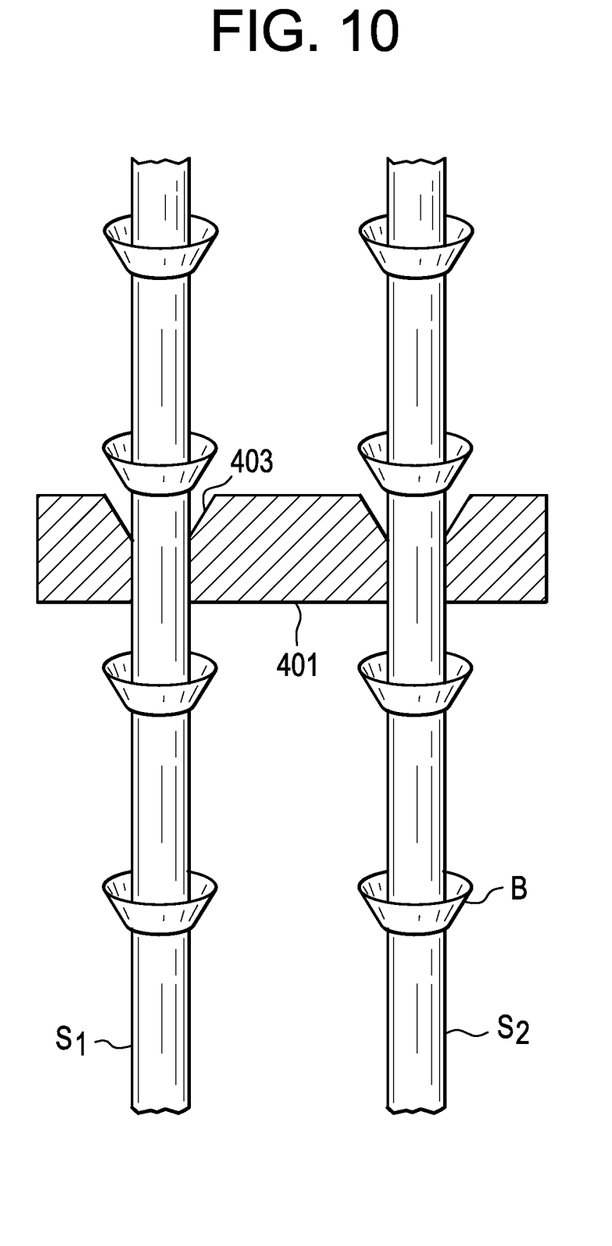
FIG. 10 shows a tie bar for securing the suture of the migration barrier.

In some embodiments, the suture is provided with a tie bar 401 slidably attached thereto, wherein at least a portion of each throughhole 403 of the tie bar slides over the suture and has a frustoconical geometry narrowing proximally. FIG. 10 shows a tie bar received on a suture of the migration barrier. The aligned frustoconcial shapes of the beads B and the throughholes 403 of the tie bar allow the tie bar to easily advance distally down the suture, but to resist its own proximal retraction. Thus, this tie bar allows the surgeon to tighten the suture upon the vertebral bodies (and thereby stabilize the cage) but prevents relaxation of the implanted suture. This procedure is amenable to being carried out through a tube.

Therefore, in accordance with the present invention, there is provided a kit for stabilizing an intervertebral disc space, comprising:

a) an intervertebral fusion cage,
    b) an expulsion barrier comprising:
        i) a plurality of suture anchors, each anchor having a hollow shaft having an inside surface forming a bore and an outside surface having a bone-engaging surface feature thereon,
        ii) a suture having a proximal end portion and a distal endportion,
        iii) a tie bar having first and second frustoconical throughholes,
    wherein the suture is threaded through the bore of each suture anchor, and
    wherein each end portion of the suture passes through a respective throughhole of the tie bar,
    wherein the tie bar is proximal to each bone anchor on the suture.

In some embodiments, the suture is provided with a tie bar slidably attached thereto, and the tie bar is made of a heat conductive, thermoplastic material. Once the anchors are strung together with the suture, the surgeon advances the tie bar distally over the suture ends to thereby tighten the suture. Next, the surgeon contacts a heat source (such as a bipolar electrode) to the thermoplastic tie bar. The energy passes quickly through the bead and heats up both the tie bar and the portion of the suture located within the tie bar. When the tie bar temperature rises to a predetermined level, it partially melts. Subsequent cooling of the tie bar causes the bead and suture to solidify and bond together, thereby forming a permanent stop against suture loosening. Thus, this thermoplastic tie bar allows the surgeon to tighten the suture upon the vertebral bodies (and thereby stabilize the cage), but prevents relaxation of the implanted suture. This procedure is amenable to be carried out through a tube.

Therefore, in accordance with the present invention, there is provided a kit for stabilizing an intervertebral disc space, comprising:

a) an intervertebral fusion cage,
    b) an expulsion barrier comprising:
        i) a plurality of suture anchors, each anchor having a hollow shaft having an inside surface forming a bore and an outside surface having a bone-engaging surface feature thereon,
        ii) a suture having a proximal end portion and a distal endportion,
        iii) a tie bar having first and second throughholes and made of a thermoplastic material,
    wherein the suture is threaded through the bore of each suture anchor, and
    wherein each end portion of the suture passes through a respective throughhole of the tie bar,
    wherein the tie bar is proximal to each bone anchor on the suture.

In some embodiments, the suture may be secured by providing a locking mechanism substantially similar to the SP-P011M Cord Lock, marketed by UMX Universal Mercantile Exchange, Inc., Walnut, Calif. This mechanisms accepts each end of the suture and holds them in a fixed relationship In other embodiments, the cord lock device takes a form substantially shown in the device 611 of FIGS. 11A-11C. The device comprises an annular body 613 having a hollow, conical insert 615 flexibly attached to its inner surface.621 by a flexible hinge portion 617. In use, the suture is threaded through the centers of the insert and annular body. When the appropriate degree of tension is achieved, boss 618 on the proximal end of the insert is pressed distally, while the distal end 620 of the annular body is pressed proximally (as shown by arrows). These competing pressures on the device produce a compressive force that forces the outer surface 619 of the insert into a taper lock with the inner surface 621 of the annular body, thereby locking the suture in place. In some embodiments, the inner surface 622 of the insert has a plurality of teeth 623 for enhanced gripping of the suture.

Figure 11A:
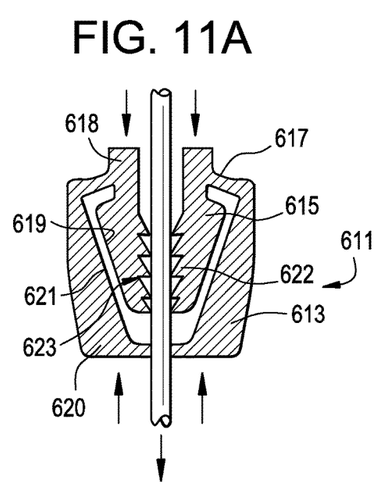
FIG. 11A discloses a cross-section of the cord lock device of the present invention.
Figure 11B:
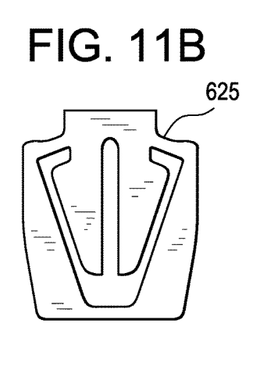
FIG. 11B discloses a side view of the cord lock device of FIG. 11A.

FIG. 11B is a side view of the cord lock device of FIG. 11A, further having a compression slot 625.

Figure 11C:
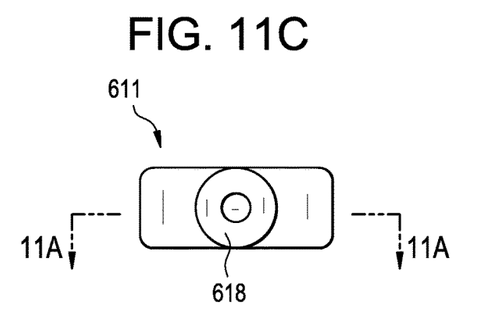
FIG. 11C discloses a top view of the cord lock device of FIG. 11A.

FIG. 11C shows a top view of the device 611. Although the view shows a substantially rectangular device, the device may be any suitable profile, including circular.

Figure 12:
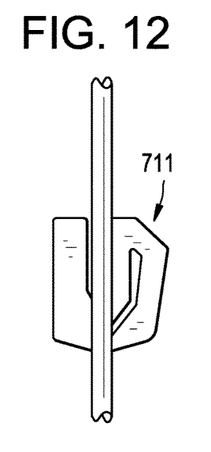
FIG. 12 discloses a second embodiment of the cord lock device of the present invention.

FIG. 12 discloses a second embodiment of the cord lock device 711 having a different taper lock configuration.

Figure 13:
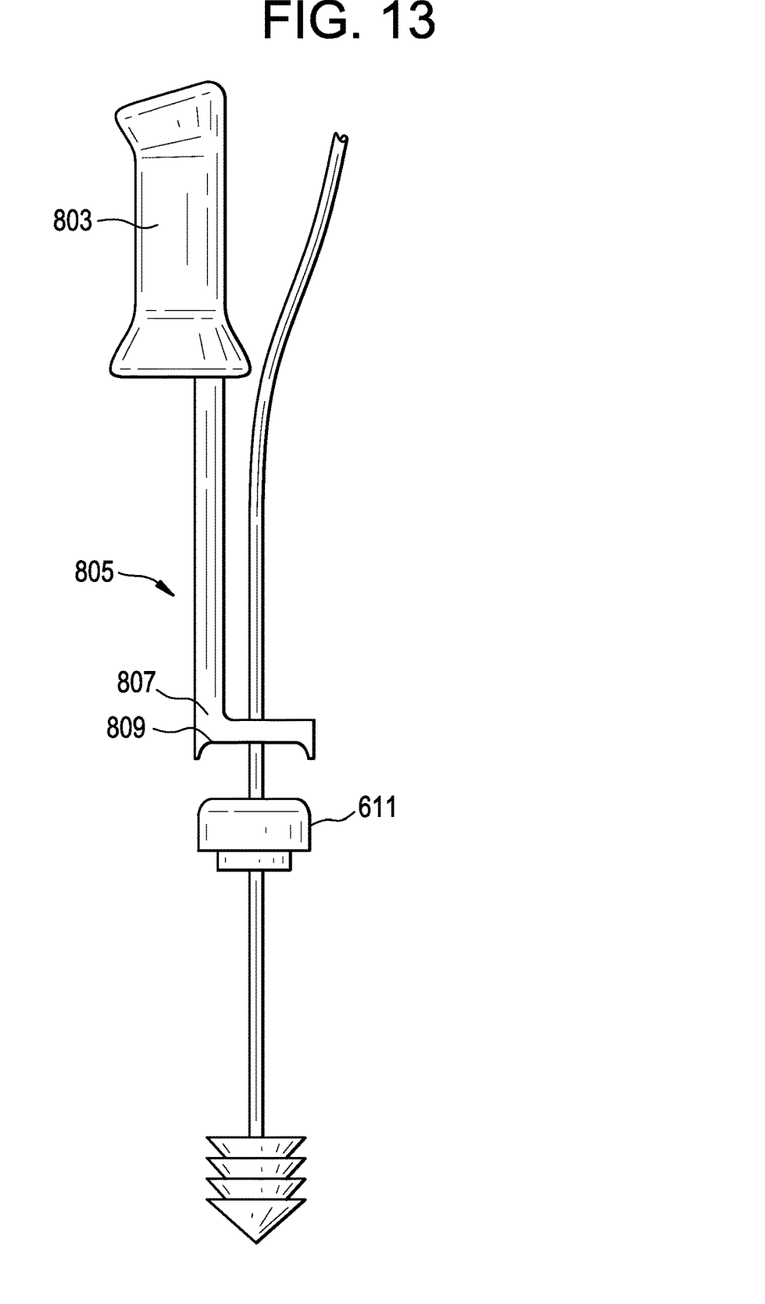
FIG. 13 discloses an instrument for assisting in the locking of the suture by a cord lock device of the present invention.

FIG. 13 discloses an instrument for assisting in the locking of the suture by a cord lock device of the present invention. The instrument 801 has a proximal handle 803, an intermediate shaft 805 and a distal end 807 having a recessed surface 809 having a hole therethrough. In use, once the suture is passed through the cord lock device and the hole of the instrument, the instrument is pressed down on the cord lock device so that the recessed surface of the instrument presses against the boss of the cord lock device. Once the cord lock device is moved distally so as to contact the last bone anchor, the resulting compressive force on the cord lock device achieves the taper lock.

I claim:

1. A kit for stabilizing an intervertebral disc space, comprising:
    a) an intervertebral fusion cage having an anterior face, an upper surface and a lower surface,
    b) an expulsion barrier comprising:
        i) a plurality of suture anchors, each suture anchor having a hollow shaft having an inside surface forming a bore, a proximal end, a distal end, and an outside surface having a bone-engaging surface feature thereon, and ii) a suture having a first end portion and a second end portion, wherein the suture is threaded through the bore of each suture anchor, and wherein the end portions of the suture contact each other to form only a single a slip-knot, wherein each suture anchor has a longitudinal axis extending in the direction defined by the proximal end of the suture anchor and the distal end of the suture anchor, and wherein the bore extends substantially in parallel with the longitudinal axis of the suture anchor, from the proximal end of the suture anchor to the distal end of the suture anchor, wherein the plurality of suture anchors define a plurality of suture segments in the suture, and wherein the expulsion barrier is disposed with respect to the cage such that each suture segment traverses the anterior face of the cage so that each suture segment passes above the upper surface of the cage and below the lower surface of the cage.

2. The kit of claim 1 wherein the slip knot is a Giant Knot.

3. The kit of claim 1 wherein the slip knot is selected from the group consisting of an SMC Knot, a Snyder Knot, a Duncan Knot, a Field Knot and a Nicky's Knot.

4. The kit of claim 1 wherein the cage has a length : width ratio of at least 2.5 : 1.

5. The kit of claim 1 wherein the bore includes a suture-engaging member extending substantially transverse to an axis of the bore and adapted to receive the suture therearound such that the suture can extend around the suture-engaging member and the end portions of the suture can extend through the bore and out of a proximal end of the hollow shaft.

* * * * *